US008859160B2

(12) United States Patent
Glipa et al.

(10) Patent No.: US 8,859,160 B2
(45) Date of Patent: Oct. 14, 2014

(54) MONOMERS AND POLYMERS CARRYING IMIDAZOLE AND BENZIMIDAZOLE GROUPINGS, AND PROTON EXCHANGE MEMBRANE CONTAINING THE SAME FOR THE PRODUCTION OF A FUEL CELL

(75) Inventors: Xavier Glipa, Verneuil sur Seine (FR); Bruno Ameduri, Montpellier (FR); Louis Delon, St Gely du Fesc (FR); Deborah Jones, St Martin de Londres (FR); Jacques Roziere, St Martin de Londres (FR); Guillaume Frutsaert, Montpellier (FR)

(73) Assignees: Peugeot Citroen Automobiles SA, Velizy Villacoublay (FR); CNRS (Centre National de la Recherche Scientifique), Paris (FR)

(*) Notice: Subject to any disclaimer, the term of this patent is extended or adjusted under 35 U.S.C. 154(b) by 1694 days.

(21) Appl. No.: 12/303,722

(22) PCT Filed: May 29, 2007

(86) PCT No.: PCT/FR2007/051348
§ 371 (c)(1),
(2), (4) Date: Sep. 22, 2009

(87) PCT Pub. No.: WO2007/121441
PCT Pub. Date: Dec. 13, 2007

(65) Prior Publication Data
US 2010/0151351 A1 Jun. 17, 2010

(30) Foreign Application Priority Data

Jun. 7, 2006 (FR) ...................................... 0652047
Jun. 7, 2006 (FR) ...................................... 0652048

(51) Int. Cl.
*C07D 233/54* (2006.01)
*C08F 226/06* (2006.01)
(Continued)

(52) U.S. Cl.
CPC ............ *C07D 233/96* (2013.01); *C08F 226/06* (2013.01); *H01M 2300/0082* (2013.01); *C08J 2327/12* (2013.01); *H01M 8/1072* (2013.01); *Y02T 90/32* (2013.01); *C25B 13/08* (2013.01); *H01M 8/103* (2013.01); *C08J 5/225* (2013.01); *C08J 2329/02* (2013.01); *C08F 214/186* (2013.01); *H01M 8/1039* (2013.01); *Y02E 60/521* (2013.01); *H01M 2250/20* (2013.01); *H01M 8/1027* (2013.01); *C07D 235/10* (2013.01); *B01D 71/62* (2013.01); *C08F 216/1458* (2013.01)
USPC .............. 429/492; 521/27; 521/31; 521/38; 548/341.1

(58) Field of Classification Search
None
See application file for complete search history.

(56) References Cited

U.S. PATENT DOCUMENTS 5,344,925 A * 9/1994 Goulet et al. ................. 540/456
6,750,352 B2    6/2004 Ono et al.

FOREIGN PATENT DOCUMENTS

FR        2877147 A    4/2006

OTHER PUBLICATIONS

Scharfenberger et al., Fuel Cells, vol. 6, Issue 3-4, Aug. 2006 (Abstract only).*
CAPlus Accession No. 2006:871981, Database entry for Scharfenberger et al., Fuel Cells, vol. 6, Issue 3-4, pp. 237-250, 2006.*
Domina et al., Izvestia Akademii Nauk SSSR. Seria Himiceskaa, Moscow, RU, vol. 9, 1979, pp. 2096-2102, XP009078697, ISSN: 0002-3353 pp. 2099-2100.
Baikalova et al., Izvestia Akademii Nauk SSSR. Seria Himiceskaa, Moscow, RU, vol. 5, 1977, pp. 1158-1161, XP00907698, ISSN: 0002-3353 p. 1160.
Savadogo, Emerging membranes for electrochemical systems—Part II. High temperature composite membranes for polymer electrolyte fuel cell (PEFC) applications, Journal of Power Sources, Elsevier, Amsterdam, NL, vol. 127, No. 1-2, Mar. 10, 2004, pp. 135-161, XP04494974, ISSN: 0378-7753.

(Continued)

*Primary Examiner* — Alicia L Otton
(74) *Attorney, Agent, or Firm* — Nicolas E. Seckel

(57) ABSTRACT

The invention relates to a monomer (6, 14) carrying an imidazole-type heterocycle (3). According to the invention, the chemical structure of said monomer (6, 14) comprises at least one unit of formula (I) wherein R1 comprises an alkenyl grouping and R2 comprises a grouping for protecting one of the nitrogen atoms of the heterocycle. The invention also relates to a monomer carrying a benzimidazole-type heterocycle, and to protected polymers obtained from said monomers, deprotected polymers produced by the protected polymers, a proton exchange membrane based on deprotected polymers, and a fuel cell provided with said membrane. Furthermore, the invention relates to methods for producing the above-mentioned monomers and polymers.

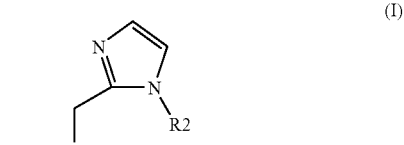

(I)

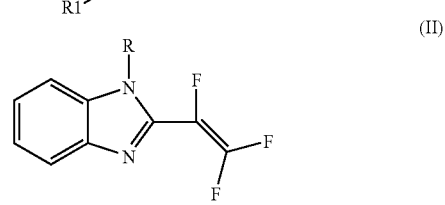

(II)

21 Claims, 10 Drawing Sheets

(51) Int. Cl.
*C08F 126/06* (2006.01)
*C08J 5/22* (2006.01)
*H01M 8/10* (2006.01)
*C07D 233/96* (2006.01)
*C25B 13/08* (2006.01)
*C08F 214/18* (2006.01)
*C07D 235/10* (2006.01)
*B01D 71/62* (2006.01)
*C08F 216/14* (2006.01)

(56) References Cited

OTHER PUBLICATIONS

Troitskaya et al., Zhurnal Organicheskoi Khimii, vol. 10, 1974, pp. 1524-1529, XP009078686, p. 1524.
International Search Report mailed Oct. 24, 2007 in PCT/FR2007/051348.

* cited by examiner

X= CF₃, Cl

X= Cl

MONOMERS AND POLYMERS CARRYING IMIDAZOLE AND BENZIMIDAZOLE GROUPINGS, AND PROTON EXCHANGE MEMBRANE CONTAINING THE SAME FOR THE PRODUCTION OF A FUEL CELL

The present invention concerns mainly monomers and polymers that can be used for the production of a proton conducting membrane in the absence of water.

The invention also concerns a method of producing these monomers and polymers, wherein the membranes can be produced from these monomers, as well as the use of these membranes as solid polymer electrolyte or as proton exchange membrane in a fuel cell.

In such a fuel cell, an electrolyte is "sandwiched" between two active layers which are the seat of anodic and cathodic reactions that ensure the conversion of chemical energy into electric energy.

According to this configuration, the electrolyte must ensure proton transfer from one active layer to the other.

To this effect, fuel cells are of the solid polymer electrolyte type (SPEFC or Solid Polymer Electrolyte Fuel Cell) or of the proton exchange membrane type (Proton Exchange Membrane Fuel Cell) and they are without doubt the most elegant in terms of design and operation.

To ensure proton transport, known membranes contain 20 to 30% water, wherein the water molecules ensure solvation of the protons, which then become extremely mobile within the membrane.

When the polymer that constitutes the membrane also has acid functions, the water molecules enable dissociation of the acid groups and of these functions, thus releasing the protons, whose transport they then provide.

As a consequence, the performances of the membranes are limited by the amount of water they contain, and a possible dehydration of the membrane can lead to interruption of the proton transport.

This dehydration can occur because of the mobility of the water molecules and/or because of the operating temperature of the fuel cell.

That is, water molecules, since they are not linked to the polymer structure of the membrane, are mobile and can thus be carried along with high proton flows through the membrane, which, as a consequence, reduces its conducting properties, until proton transport is completely interrupted.

Only additional measures could make it possible to avoid dehydration due to the mobility of the water molecules, but these measures are detrimental in that they involve an extra cost and they make the fuel cell system more complicated (auxiliaries dedicated to humidification).

Further, there is a limit operating temperature for fuel cells, which corresponds naturally to the boiling temperature of water, i.e., 100° C. at atmospheric pressure.

This temperature constitutes a physical limit, beyond which the amount of water is considerably reduced, until the membrane is completely dried out.

A solution that would accord very well with the laws of thermodynamics would be to increase the operating pressure of the system, so as to increase the boiling temperature of water accordingly.

However, this solution is not satisfactory, because for high operating pressures, the flux of protons crossing the membrane carries along a correspondingly an increased amount of water molecules, which ends up penalizing the performances of the fuel cell.

Most polymers constituting ionomeric membranes used in fuel cells have $SO_3H$, $PO_3H_2$ proton groups. These functional groups are dissociated in the presence of water, or in the presence of basic molecules or functional groups. When these basic groups have different proton-giving or proton-accepting sites, they can play a role identical to that of water molecules in proton transport. However, in this type of membranes, elution problems can occur during operation of the fuel cell.

In this context, a main objective of the invention is to remedy the above-mentioned drawbacks by providing a membrane that ensures proton transport at operating temperatures above 100° C. and whose production method has a high output.

To this effect, the membrane according to the invention is made from a heterocyclic polymer comprising heterocycles that ensure proton transport within the membrane, including in the absence of water. Thus, migration of the protons is ensured via heterocycles that have an additional advantage, as compared to water molecules, in that these heterocycles are anchored within the membrane, thus avoiding any elution problem.

More precisely, the invention relates to a monomer carrying a heterocycle of the imidazole type, which can be used for the production of an ionic conductive membrane, and whose chemical structure comprises at least one unit of the formula:

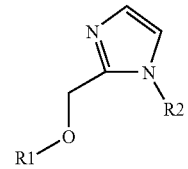

wherein R1 comprises an alkenyl group, and wherein R2 comprises a protection group of one of the nitrogen atoms of the heterocycle, such as a benzyl or trialkylsilyl group.

In a variant embodiment, R1 has the chemical formula $CH=CH_2$.

In another variant embodiment, R1 has the chemical formula $(CH_2)_2—O—CH=CH_2$.

In addition, the method of producing the polymer constituting the membrane according to the invention consists of producing a monomer provided with a heterocycle of the imidazole type and with a protection group of one of the nitrogen atoms of this heterocycle, polymerizing this protected monomer to obtain a protected polymer, subjecting this protected polymer to a step of deprotecting the nitrogen atoms of the heterocycles, via which a proton conducting polymer is obtained, and this method has a high output.

The invention also relates to a monomer of the benzimidazole type, which can be used to produce an ionic conductive membrane.

According to the invention, the chemical structure of this monomer comprises at least one unit of the formula:

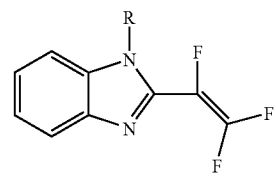

wherein R is a protection group of one of the nitrogen atoms of the heterocycle.

In addition, the method of producing the polymer constituting the membrane according to the invention consists of producing a monomer provided with a heterocycle of the benzimidazole type and with a protection group of one of the nitrogen atoms of the heterocycle, polymerizing this protected monomer to obtain a protected polymer, subjecting this protected polymer to a step of deprotecting the nitrogen atoms of the heterocycles, via which a proton conducting membrane is obtained, and this method has a high output.

This method comprises:

at least one step of reacting a compound comprising an ortho-phenylene diamine with a fluorinated monomer in the presence of an organic solvent, via which an intermediate fluorinated molecule carrying an heterocycle of the benzimidazole type is obtained, at least one step of protecting a nitrogen atom of the benzimidazole group of the intermediate molecule by a group R such as a benzyl group or a trialkylsilyl (R1R2R3Si) group or a carbamate ($CO_2R4$) group, at least one step of dehydrofluorinating the compound obtained in the previous step by reacting this compound with a base.

According to another characteristic, the invention relates to a protected polymer comprising the protected monomer as a unit, as well as to the method of producing this protected polymer.

According to a characteristic, the protected polymer is obtained by radical homopolymerization of the protected monomer or by copolymerization of the protected monomer with fluorinated monomers such as hexafluoropropene, chlorotrifluoroethylene, vinylidene fluoride, tetrafluoroethylene, trifluoroethylene, vinyl fluoride, 2H-1,1,3,3,3-pentafluoroethylene, or perfluoroalkyl vinyl ethers.

The invention also relates to the deprotected polymer made from the protected polymer, as well as to the method of producing this polymer, comprising a step of deprotecting the nitrogen atoms via which the protection groups of the polymer are replaced by hydrogen atoms, so as to form a deprotected polymer provided with heterocycles of the benzimidazole type.

The invention also concerns the ionic conductive membrane made from the deprotected polymer, the fuel cell implementing this ionic conductive membrane as electrolyte, and the electrolyzer comprising a cell implementing this same membrane as electrolyte.

The invention will be better understood and other objectives, advantages and characteristics of the invention will appear clearly by reading the following description made in reference to the annexed drawings in which.

The present invention proposes to produce particular polymers forming membranes that make it possible to have proton conduction properties even at temperatures higher than 100° C., such as 200° C., at atmospheric pressure.

Migration of the protons is ensured via heterocycles 2, which are immobilized and anchored to the polymer structure of the membrane.

In this way, the heterocycles 2 do not accompany the proton in its migration, even for high proton fluxes, and thus, they maintain complete effectiveness of the fuel cell, including at high temperature.

Figure 1:
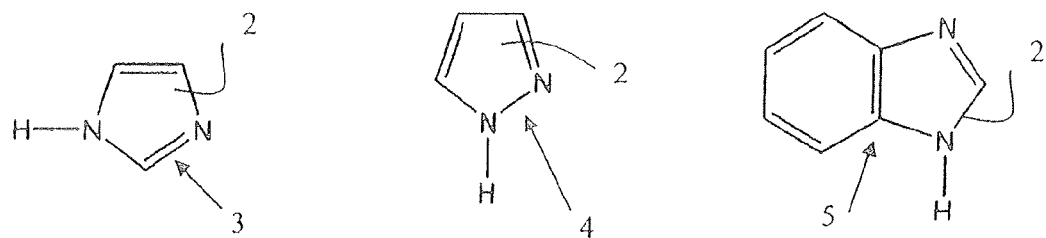
FIG. 1 represents examples of heterocycles that can be integrated to the polymer according to the invention.

Thus, the approach is based on the use of heterocycles 2 such as imidazoles 3, pyrazoles 4, benzimidazoles 5, illustrated on FIG. 1, as solvents for the protons, as a replacement for the water molecules of known membranes.

That is, just like water, these heterocycles 2 form networks of hydrogen bonds, and they have proton transporting properties similar to those of water.

In such an environment of immobilized heterocycles 2, proton transport relies essentially on a known diffusion mechanism, of the Grotthuss type, that involves transfer of the proton between heterocycles 2 and their reorganization, for example, by reorientation.

Numerous types of polymers carrying heterocycles 2 can be synthesized, and in the following, a family of polymers comprising imidazole heterocycles 3, as well as various method that make their production possible, are described in detail.

A first method of producing this polymer consists of cationic homopolymerization of monomers containing imidazole 6, such as 1-benzyl-2-(vinyloxyethyloxymethyl)imidazoles 6 by using initiators of the type $ZnI_2$, $HgI_2$ or any other iodized complex or even Crivello salts.

Figure 2:
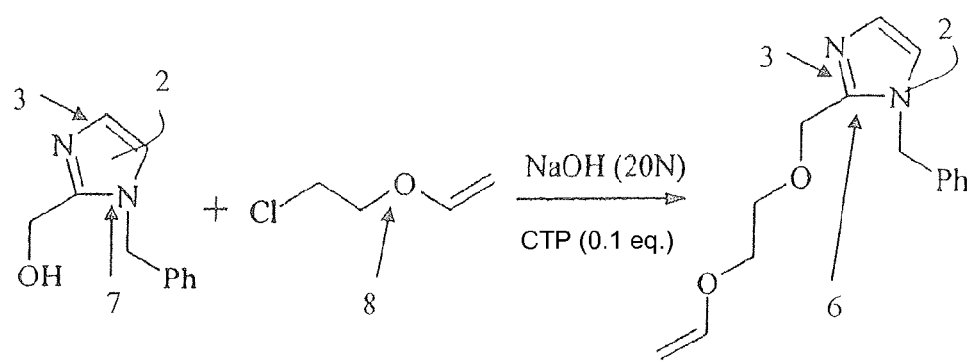
FIG. 2 illustrates the synthesis of a first monomer having a heterocycle of the imidazole type according to the invention.

The synthesis of this monomer 6, represented on FIG. 2, is performed by phase transfer catalysis by reaction of an intermediate molecule 7, such as 1-benzyl-2-(hydroxymethyl) imidazole 7, with 2-chloroethyl vinyl ether 8.

The phase transfer catalyst used in this reaction is benzyl triethyl ammonium chloride and the output varies between 85 and 90%.

Figure 3:
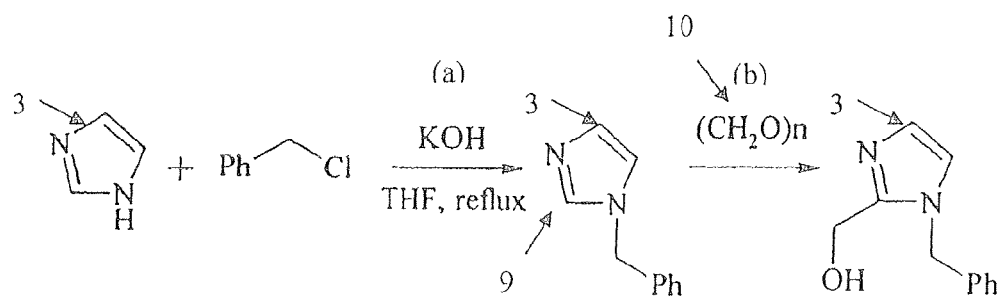
FIG. 3 shows the synthesis of an intermediate molecule that plays a role as reagent in the reaction of FIG. 2.

The step of formation of the intermediate molecule 7, known by the person of the art, is represented on FIG. 3, and consists of a reaction between 1-benzylimidazole 9 and formaldehyde or paraformaldehyde 10.

Thus, by the above-mentioned cationic homopolymerization of the monomer 6, a polymer is obtained, on which imidazole heterocycles 3 are anchored, whose nitrogen atoms are protected by a benzyl group and can be deprotected by reaction of the polymer with $Pd(OH)_2$.

Figure 4:
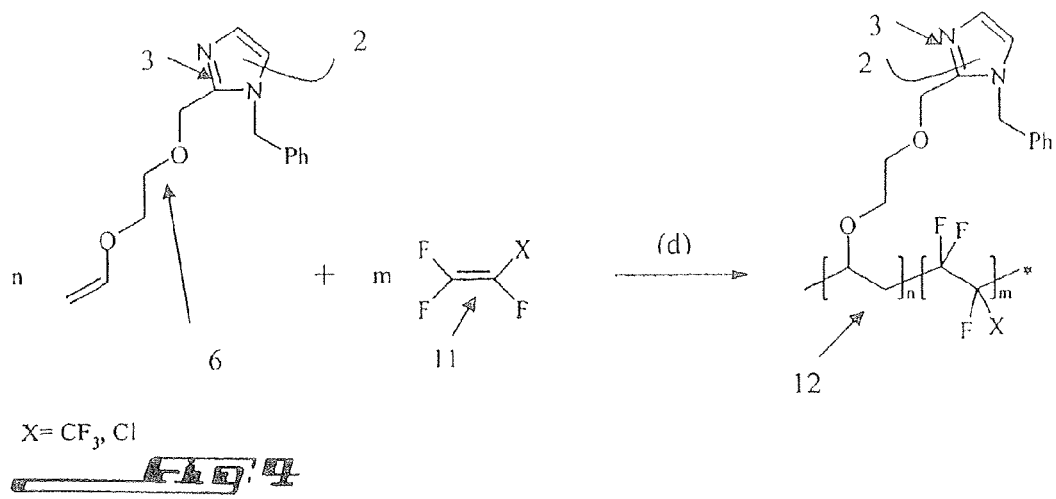
FIG. 4 represents the synthesis of a polymer according to the invention from the first monomer of FIG. 2.

A second method of producing a polymer containing imidazole 3 according to the invention consists of a radical copolymerization, represented on FIG. 4, of the above-described monomer 6 with fluorinated monomers 11, such as tetrafluoroethylene (TFE), hexafluoropropene (HFP, $X=CF_3$), and/or chlorotrifluoroethylene (CTFE, $C=Cl$), or bromorotrifluoroethylene (XTFE, $X=Br$), trifluoroethylene, pentafluoropropene, 3,3,3-trifluoropropene, perfluoro methyl vinyl ether (PMVE), perfluoro ethyl vinyl ether (PEVE), perfluoro propyl vinyl ether (PPVE), from which a first fluorinated polymer 12 carrying imidazole 3 functions is obtained.

The radical copolymerization is performed with radical initiators of the type peroxides, azo, peroxycarbonates, or peroxypivalates in an autoclave at a pressure comprised between 5 and 50 bar, at a temperature determined as a function of the nature of the initiator used, so that at this temperature, the initiator has a half-life of about 1 hour.

This polymer 12 thus formed has been characterized in particular thanks to $^{19}F$ and $^1H$ nuclear magnetic resonance spectroscopy by analysis of the copolymerization reaction product, after evaporation of the solvent and purification by precipitation in pentane.

Figure 5:
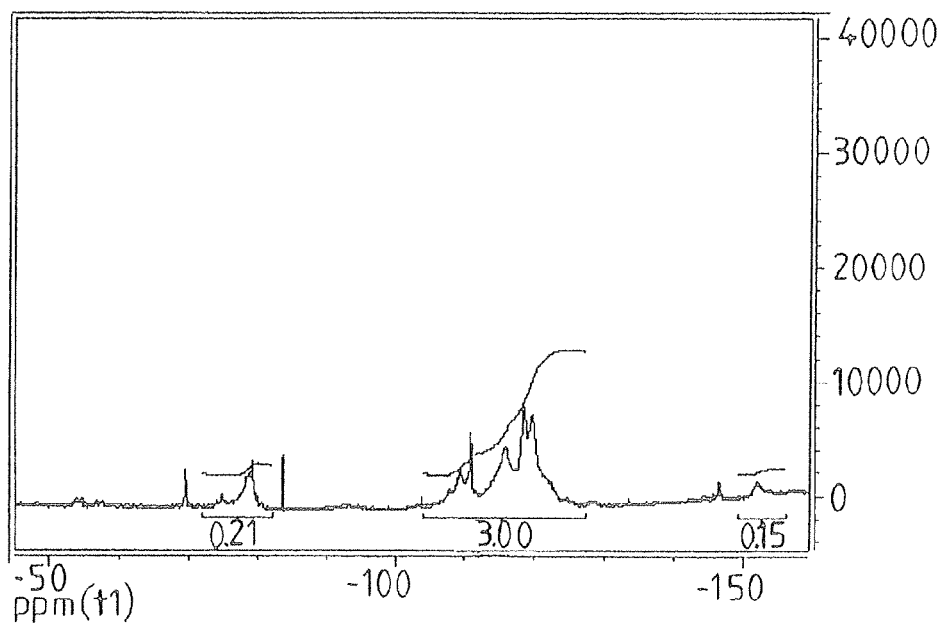
FIG. 5 illustrates the $^{19}F$ NMR characterization of the polymer of FIG. 4.

The $^{19}F$ NMR spectrum obtained (FIG. 5) confirms that the fluorinated copolymer 12 is obtained.

That is, the complex signals visible on this spectrum, located between −70 and −85 ppm and between −108 and −125 ppm, are characteristic of the chemical displacement of the fluorine atoms of the chlorotrifluoroethylene (CTFE) units in the CTFE-vinyl ether copolymer.

Figure 6:
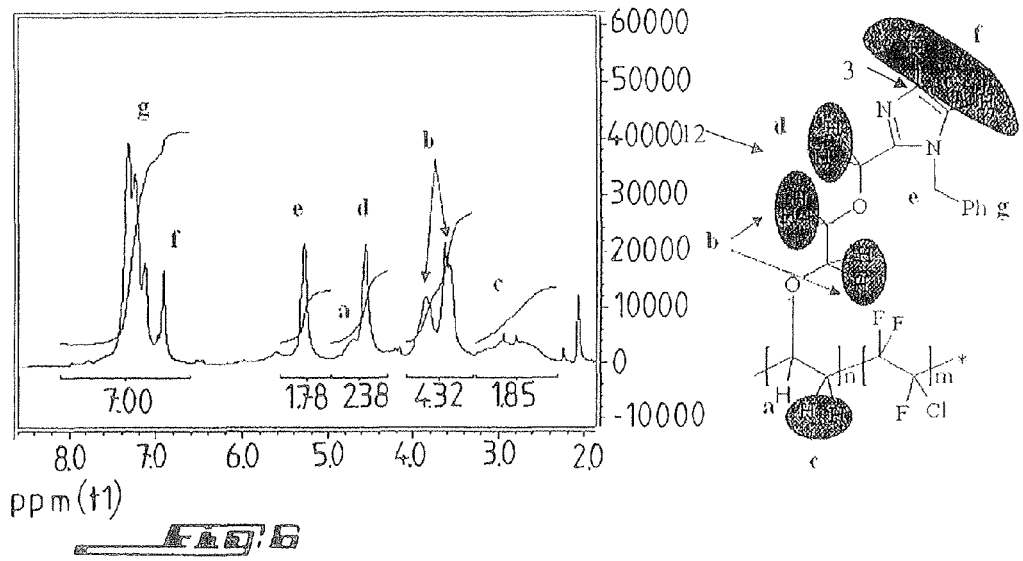
FIG. 6 represents the $^1H$ NMR characterization of the polymer of FIG. 4.

Further, the $^1H$ NMR spectrum confirms the incorporation of the monomer 6 into the polymer 12 (FIG. 6) and the absence of a transfer to the monomer, solvent, initiator, and polymer.

The polymer 12 is thus constituted by a succession of monomers containing imidazole 6 which have each a protection group of the nitrogen atom, that is, a benzyl group.

Figure 7:
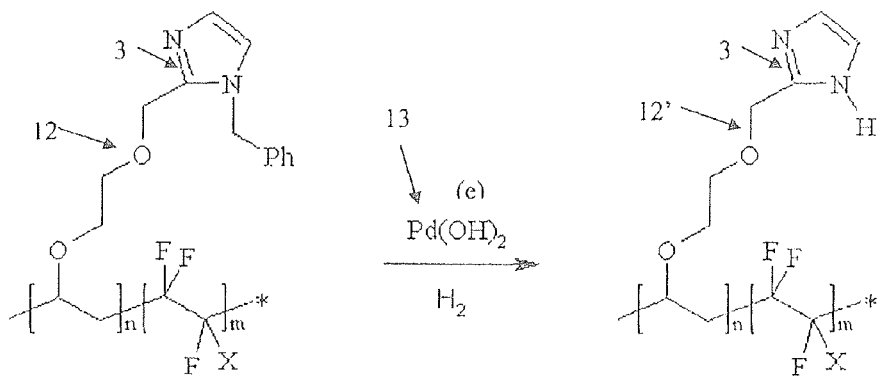
FIG. 7 illustrates the formation of a second imidazole-containing polymer.

The protected polymer 12 thus obtained is subjected to a deprotection step represented on FIG. 7, during which the benzyl protection groups are replaced by hydrogen atoms, so as to form imidazole groups which will ensure proton conduction.

This deprotection step consists of a reaction of the first polymer 12 in the presence of dihydrogen and palladium dihydroxide $Pd(OH)_2$ 13.

The deprotected polymer 12' thus obtained is similar to the first polymer 12, but it comprises a hydrogen atom as a replacement for the benzyl group of the first polymer 12, and as a consequence, it has proton conducting properties.

For informational purposes, the detail of experiments conducted with a view at the formation of the deprotected polymer 12' is described below:

Synthesis of 1-benzylimidazole 9 illustrated by step (a) of FIG. 3.

According to the selected experimental protocol, 44 g of imidazole (0.65 mol.), 100 g of benzyl chloride (0.78 mol.), and 60 g of KOH (1.07 mol.) in 700 ml of THF are placed in a 1-liter balloon flask. The reaction mixture is brought to reflux for 120 h, then cooled at ambient temperature. The organic phase is filtered and the solvent is evaporated under reduced pressure. The obtained solid product is dissolved in 500 ml of $CH_2Cl_2$, then washed with water (3×100 ml). The organic phase is dried on $Na_2SO4$, filtered, then evaporated under reduced pressure. The collected solid is recristallized in toluene to yield 67 g of desired product.

Synthesis of 1-benzyl-2-hydroxymethyl-imidazole 7 represented by step (b) on FIG. 3

50 g of 1-benzyl-imidazole from the raw product of the previous reaction and 15 g of paraformaldehyde are dissolved in 150 ml of dioxane. The mixture is brought to 135° C. in autoclave for 20 h. The solvent is evaporated under reduced pressure, the obtained product in the form of a black oil is dissolved in 400 ml of $CH_2Cl_2$, then washed with water (2×100 ml). The organic phase is dried on $Na_2SO_4$, filtered, then evaporated under reduced pressure. The product is drawn under a vacuum for 24 h, then recristallized in 100 ml of ethyl acetate to yield 30 g of pure product (output=50% from the imidazole).

Figure 11:
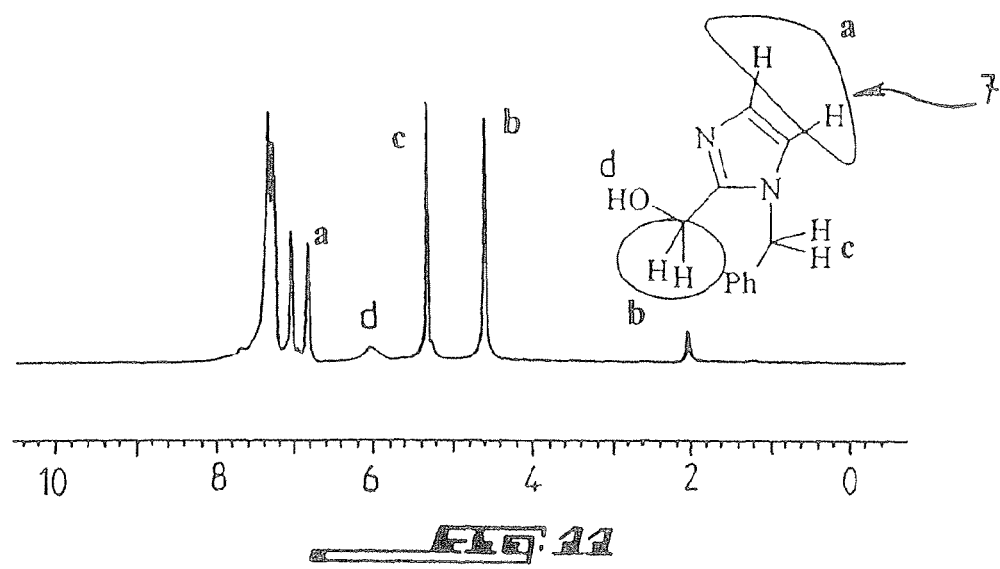
FIG. 11 illustrates the $^1H$ NMR spectrum obtained for the intermediate molecule 7.

The $^1H$ NMR spectrum obtained for the final product, visible on FIG. 11, confirms that 1-benzyl-2-hydroxymethyl-imidazole 7 is obtained.

Synthesis of 1-benzyl-2-(vinyloxyethyloxymethyl)imidazole 6 represented by FIG. 2

0.54 g of TEBAC ($2.4×10^{-3}$ mol) and 5.6 g of CEVE (0.05 mol) are added to a solution of 1-benzyl-2-hydroxymethylimidazole (4.7 g, 0.024 mol.) in toluene (15 ml). A basic solution 20 N in NaOH (100 ml) is then added in the medium and the heterogeneous mixture is brought to 90° C. for 24 h with vigorous stirring. After cooling, the solution is diluted with 250 ml of decanted ether, then the organic phase is washed with water until pH=7 (10×100 ml). The organic phase is dried on $Na_2SO_4$, filtered, then evaporated under reduced pressure to yield 5.3 g (85%) of desired product. Given the satisfactory purity of the obtained product, no further purification is required.

Figure 13:
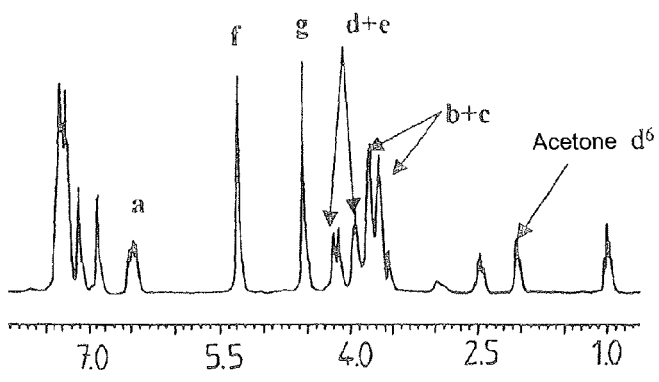
FIG. 13 represents the $^1H$ NMR spectrum obtained for the monomer of FIG. 12.
Figure 13:
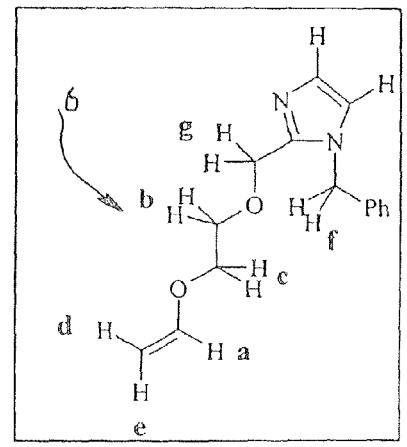

The $^1H$ NMR spectrum of the obtained product, represented on FIG. 13, confirms that 1-benzyl-2-(vinyloxyethyloxymethyl)imidazole 6 is obtained.

Synthesis of the copolymer poly(E.V-alt-CTFE) or protected polymer 12 illustrated by step (d) on FIG. 4

The copolymerization of 1-benzyl-2-(vinyloxyethyloxymethyl) imidazole 6 with CTFE is performed in a 100 $cm^3$ autoclave in hastelloy equipped with a magnetic stirrer bar, two valves (gas input and output), a security disk, a precision manometer and a thermometer.

The autoclave is first purged of the air it contains by means of a high vacuum. 10 g of the liquid monomer (vinyl ether having the protected imidazole group), 0.210 g of tertio butyl peroxypivalate initiator and 60 ml of 1,1,1,3,3-pentafluorobutane are introduced into the system.

The combination is then cooled in an acetone bath at −80° C. and 10.1 g of CTFE are introduced into the system. The autoclave is finally placed in an oil bath at 75° C. for 14 hours, the pressure reaches 15 bar at the beginning of the manipulation to finish at 12 bar after 14 hours.

The system is then left to revert to ambient temperature, the CTFE that did not react is purged, and the raw reaction product is evaporated to obtain a viscous black oil. The brown product is solubilized in dichloromethane, then precipitated in pentane to obtain an orange-colored powder.

Deprotection of the imidazoles of the copolymer poly(E.V-alt-CTFE) by hydrogenation visible on FIG. 7 (step (e))

In the same autoclave as that used previously, 100 ml of acetic acid, 4 g of copolymer poly(E.V-alt-CTFE) and 1 g of a catalyst of the type palladium dihydroxide are introduced. The autoclave is then closed and 32 bars of hydrogen are introduced therein. The reaction mixture is heated at 70° C. for 48 hours. The raw reaction product is filtered on celite, then the solvent is evaporated. The obtained product is refluxed in 50 ml of a 5% $Na_2CO_3$ solution. The product is filtered, washed with three times 50 ml of distilled water, then dried. Finally, it is taken up in methanol and precipitated in ether. 2 g of orange solid is obtained with a deprotection rate of 90%.

Analyses performed on the final product show that this final product has a glass transition temperature of −33° C. and a thermal stability of up to 200° C. for an average molecular mass of 8,500 $g·mol^{-1}$ (PMMA equivalent).

Figure 12:
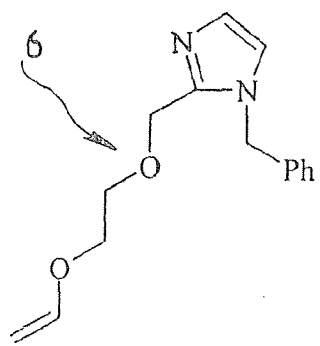
FIG. 12 is an illustration of the first monomer according to the invention.

These steps make it possible to form a proton conducting polymer having the monomer 6 of FIG. 12 as a unit.

It is possible to prepare a polymer containing imidazole groups 3 according to a third production method consisting of polymerization of a second imidazole-containing monomer 14, which is 1-benzyl-2-(vinyloxymethyl)imidazole.

Figure 8:
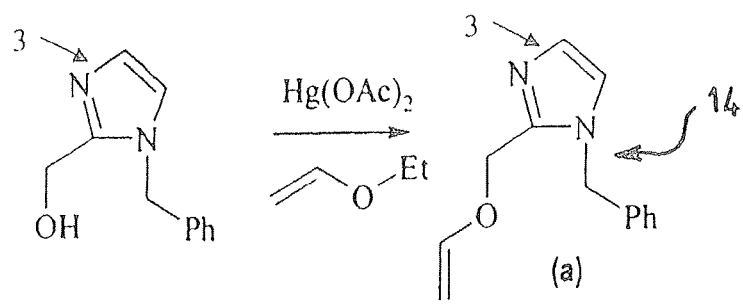
FIG. 8 shows the formation of a second monomer having a heterocycle of the imidazole type.
Figure 9:
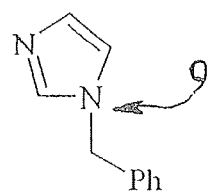
FIG. 9 is an illustration of the 1-benzimidazole 9 of FIG. 3.
Figure 10:
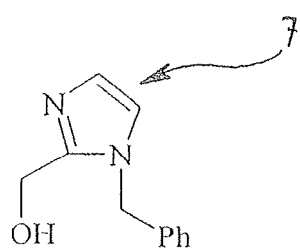
FIG. 10 represents the intermediate molecule 7 of FIG. 3.

As is visible on FIG. 8, synthesis of this monomer 14 consists of a transetherification reaction of the intermediate molecule 7 of FIG. 3 by ethyl vinyl ether 15, in the presence of transetherification catalysts such as palladium acetate (Pd $(OAc)_2$ or mercury acetate $(Hg(OAc)_2$ 16.

Subsequently, this monomer 14 is polymerized, either by homopolymerization as described above in reference to the first method, or by copolymerization with fluorinated monomers 11 as described in reference to the second method, from which results the formation of an imidazole-containing protected polymer, which is fluorinated or not.

As described for the above-described first and second methods, the polymer obtained by the third method can react with $Pd(OH)_2$ to obtain a deprotected polymer, i.e., which is without benzyl groups and has proton conducting properties.

A fourth method of forming the polymer according to the invention can consist of terpolymerization of one or the other of the monomers 6 and 14 described above and illustrated on FIGS. 2 and 8, respectively, with two fluorinated alkenes, selected among tetrafluoroethylene (TFE), hexafluoropropene (HFP, $X=CF_3$) and/or chlorotrifluoroethylene (CTFE, X—Cl), or bromotrifluoroethylene (XTFE, X=Br), trifluoroethylene, pentafluoropropene, 3,3,3-trifluoropropene, perfluoro alkyl methyl vinyl ether (PMVE), perfluoro alkyl ethyl vinyl ether (PEVE), perfluoro alkyl propyl vinyl ether (PPVE) or any other analogous molecule having a longer fluorinated chain.

As for the polymers produced by the above methods, the polymer obtained by the fourth method can be deprotected by reaction with $Pd(OH)_2$ and form a proton conducting polymer.

The various deprotected polymers obtained from the four above-described methods can constitute the basis of proton conducting membranes.

It will be noted that various monomers having imidazole function can be produced according to a production method similar to the first method of producing the monomer 6, but in which the chloroethyl vinyl ether reagent 8 would be replaced by, for example, a compound having a longer chain and comprising such a chloroethyl vinyl ether 8.

Similarly, other monomers according to the invention can be obtained by means of a method similar to the second method of producing the monomer 14, in which the ethyl vinyl ether reagent 15 would be replaced, in particular, by a compound having a longer chain and comprising this ethyl vinyl ether 15.

Thus, other polymers than those described above can be produced from these monomers and constitute various ionic conductive membranes, which will be capable of serving as electrolytes in various electrochemical devices such as an electrolyzer or a fuel cell used, for example, to power the motion of a motor vehicle.

The membrane according to the invention used in a fuel cell makes it possible to go beyond the limit operating temperature of fuel cells with known polymeric solid electrolyte, to reduce the complexity of the fuel cell system (fuel cell and its auxiliaries), and consequently, to reduce its cost (auxiliaries dedicated to humidification are no longer necessary).

The heterocycles of the deprotected polymers formed according to the above-mentioned production methods ensure proton transport within the membrane, while the fluorinated groups present within the polymer according to some production methods (copolymerization with fluorinated alkenes, or monomer carrying fluorinated heterocycles) provide the polymer with a certain chemical inertia in an oxidizing or reducing medium, and with thermostability, which participate in the stabilization of the membrane during operation, in particular, when used in a fuel cell operating at temperatures above 100° C.

Other types of polymers carrying heterocycles 2 can be synthesized, and a family of polymers according to the invention comprising benzimidazoles heterocycles 20 will be described in detail below.

The production of a polymer provided with benzimidazole heterocycles 20 is obtained from the polymerization of benzimidazole-containing monomers.

This polymerization can consist of radical homopolymerization of benzimidazole-containing monomers, using radical initiators of the type peroxides, azo, peroxycarbonates or peroxypivalates, or of radical copolymerization of this monomer with fluorinated monomers, such as tetrafluoroethylene, trifluoroethylene, hexafluoropropene (HFP, $X=CF_3$) and/or chlorotrifluoroethylene (CTFE, X=Cl), vinyl fluoride, 2H-1, 1,3,3,3-pentafluoroethylene, vinylidene fluoride, or any perfluoro alkyl vinyl ether whose alkyl chain comprises between 1 and 20 carbon atoms.

Various methods of producing benzimidazole-containing monomers that can be used to produce the polymer according to the invention are described below.

Figure 14:
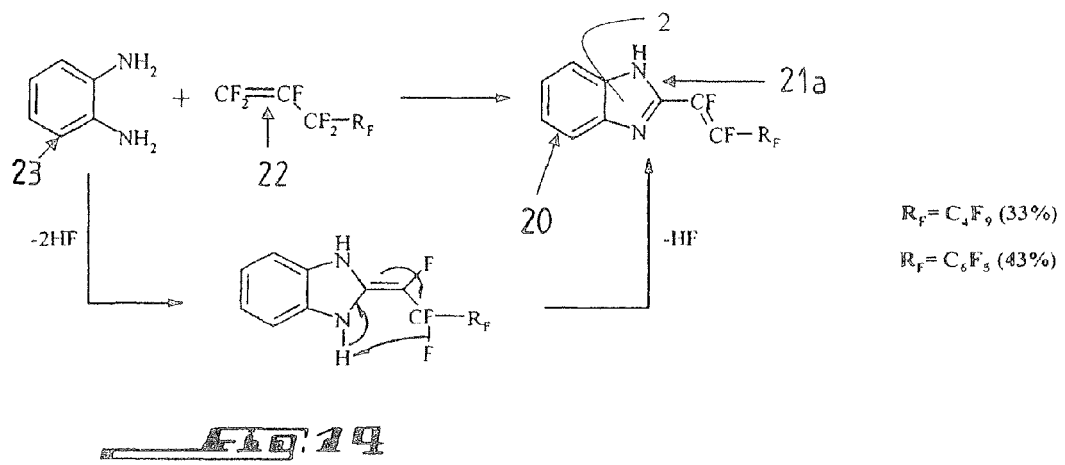
FIG. 14 illustrates a reaction known by the person of the art for producing a fluorinated benzimidazole-containing monomer.

As illustrated on FIG. 14, such a monomer 21a can be obtained by a first method known of the person of the art between a perfluorinated olefin 22 and an ortho phenylene diamine 23, this monomer 21a comprising a group $R_F$ that can be a $C_4F_9$ or $C_6F_5$ group.

However, the output of this reaction is very low.

Figure 16:
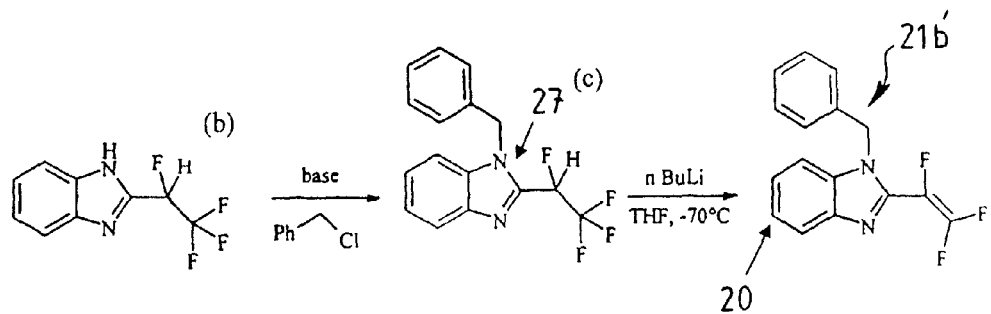
FIG. 16 shows the second (b) and third (c) steps of the method of producing the first protected monomer of the invention.

A second method of producing a benzimidazole-containing monomer whose reaction output is higher consists of synthesis of a second benzimidazole-containing monomer 21b', similar to the above-mentioned monomer 21a but without the $R_F$ group of this monomer, and further comprising, as is visible on FIG. 16, an element protecting one of its nitrogen atoms, such as a benzyl group grafted on this atom.

Figure 15:
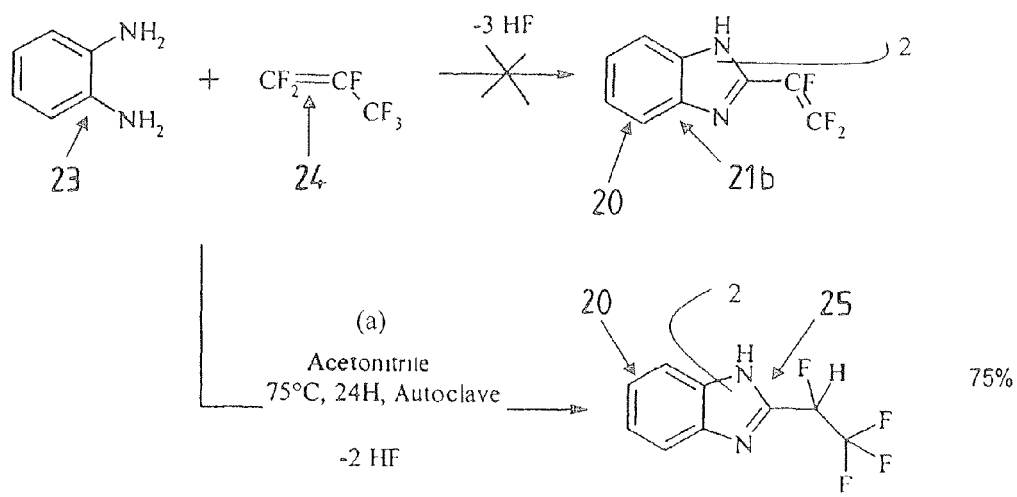
FIG. 15 illustrates the first step (a) of producing a first protected monomer according to the invention.

This second monomer 21b' is obtained in three steps illustrated on FIGS. 15 and 16, respectively.

The first step (a) illustrated on FIG. 15 is a reaction between ortho phenylene diamine 23 and hexafluoropropene 24 in autoclave for 24 hours and the resulting derived product is obtained with a good output (75%). This reaction does not make it possible to obtain a fluorinated vinyl monomer with benzimidazole functionality 21b, but to obtain 2-(1,1,1,2-tetrafluoroethyl)benzimidazole 10, after recrystallization in a water/ethanol mixture and with an output of 75%.

The second step (b), described on FIG. 16, consists of deprotection of the benzimidazole group of the 2-(1,1,1,2-tetrafluoroethyl)benzimidazole 25 performed by reaction of this compound 26 with benzyl chloride in the presence of a base, via which an intermediate compound 27 is obtained, in which the hydrogen atom of one of the nitrogen atoms of the benzimidazole groups is replaced by a benzyl group.

The third step (c) is a dehydrofluorination of this intermediate product 27 by means of butyl lithium 13 in the presence of THF (tetrahydrofurane) and at a temperature close to −70° C., thanks to which a protected monomer 21b' is obtained.

The detail of the experiments of the above-mentioned three steps (a), (b), and (c) is given below:

Step (a): Synthesis of 2-(1,2,2,2-tetrafluoroethyl)-benzimidazole 25

20 grams of ortho phenylene diamine (0.185 mol.) are dissolved in 80 ml of ethyl acetate and placed in an autoclave equipped with a manometer, two valves (input and output), and a rupture disk, preliminarily under vacuum/nitrogen cycles.

41.6 grams of hexafluoropropene (HFP) (0.277 mol.) are then introduced at ambient temperature in the autoclave.

The medium is brought to 75° C. and the pressure in the reactor is then close to 13 bar. After 18 hours of reaction, the pressure in the reactor is close to 4 bar, and the autoclave is cooled, degassed at 0° C., then the solvent is evaporated under reduced pressure.

The brown-green solid obtained is taken up in 100 ml water, neutralized by means of a $Na_2CO_3$ solution (10% by mass) until the pH of the obtained solution is equal to 7. The formed precipitate is filtered, dried in a vacuum, then recrystallized in an $H_2O$/EtOH mixture to yield 27 g (75%) of the desired intermediate 10.

Step (b): Synthesis of 1-benzyl-2-(1,2,2,2-tetrafluoroethyl)-benzimidazole 10

10 grams of 2-(1,2,2,2-tetrafluoroethyl)-benzimidazole 25 (0.05 mol.) whose synthesis is described above, and 7.3 grams of benzyl chloride (0.05 mol) are dissolved in 140 ml of $CH_3CN$.

5.2 grams of $K_2CO_3$ (0.037 mol) are then added and the reaction medium is refluxed for 48 hours.

The solvent is filtered, then evaporated under reduced pressure.

The black oil obtained is dissolved in 150 ml of $CH_2Cl_2$, washed with water (2 times 50 ml), dried on $Na_2SO_4$, filtered, then evaporated under reduced pressure.

The obtained product is dissolved again in 15 ml of ethyl acetate, precipitated in 200 ml of heptane, filtered, then the filtration product is evaporated under reduced pressure.

The 9 grams of light-yellow product collected are recrystallized in 15 ml of hexane to yield 6.3 g (43%) of pure product 27 (light-yellow powder).

Step (c): Synthesis of 1-benzyl-2-(1,2,2-trifluorovinyl)-benzimidazole 21b'

In a 100 ml Schlenk flask that was previously purged with nitrogen, 3 grams of 1-benzyl-2-(1,2,2,2-tetrafluoroethyl)-benzimidazole 27 (0.01 mol.) are dissolved in 50 ml of tetrafhydrofurane (THF) that was previously dried on calcium hydride, then freshly distilled in argon.

The system is cooled to −78° C. in a light flow of nitrogen, then 6.5 ml of n-BuLi (1.6 M in hexane, 0.01 mol.) are added drop by drop.

The reaction medium is then maintained at low temperature for 1 hour, then left at ambient temperature with stirring for 24 hour.

Finally, 5 ml of EtOH are added at the end of the reaction, then the solvent is evaporated under reduced pressure. The product is taken up in 40 ml of $CH_2Cl_2$, washed with water (2 times 20 ml), dried on $Na_2SO_4$, then the solvent is evaporated under reduced pressure.

Figure 17:
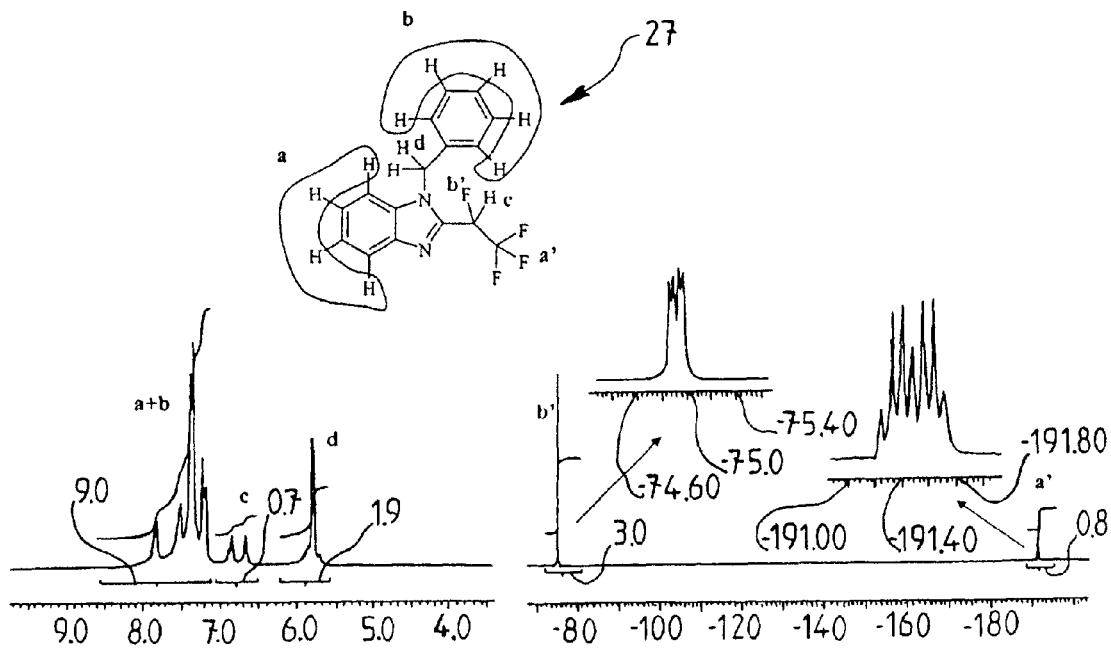
FIG. 17 represents the $^{19}F$ and $^2H$ NMR spectra obtained for the monomer formed in step (c) of FIG. 16.

The $^1H$ and $^{19}F$ NMR spectra illustrated on FIG. 17 confirm that the desired compound is obtained, since they show the presence of the protons of the benzyl protection group as well as that of the protons of the benzimidazole heterocycle ($^1H$ NMR), and the presence of the perfluorinated double-bond of this monomer, respectively, given that the doublets of doublets of doublets characteristics of this bond, centered at −105, −124, and −175 ppm, can be observed on the $^{19}F$ NMR spectrum that.

The monomer 21b' obtained at the end of this step (c) can be homopolymerized by radical initiation or copolymerized with fluorinated olefins such as tetrafluoroethylene, trifluoroethylene, vinyl fluoride, 2H-1,1,3,3,3-pentafluoroethylene, hexafluoropropene (HFP), chlorotrifluoroethylene (CTFE) or vinylidene fluoride (VDF), in order to obtain a protected polymer which will necessarily be fluorinated.

Figure 18:
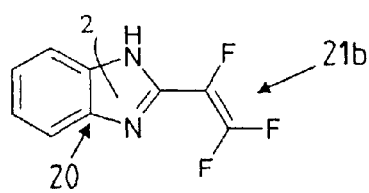
FIG. 18 represents a second monomer including benzimidazole.

After having obtained this polymer, it is possible to perform the deprotection of the nitrogen atoms carrying the protecting benzyl group, via which a deprotected polymer is obtained, whose unit is constituted by the monomer 21b of FIG. 18, named 2-(1,2,2-trifluorovinyl)-benzimidazole.

This polymer with deprotected nitrogen atoms, i.e., carrying a nitrogen atom and no longer a protection group, consequently has proton-conducting properties.

In the following, synthesis of a monomer 21c' similar to the monomer 21b' described above, but comprising another protection group for the nitrogen atom of the benzimidazole group, is described.

More precisely, the monomer 21c' has, as a protection element a compound R that can be a trialkylsilyl (R1R2R3Si) group or a carbamate group ($CO_2R4$) in which the groups R1 to R4 can be constituted by alkyl chains having from 1 to 20 carbon atoms.

Figure 19:
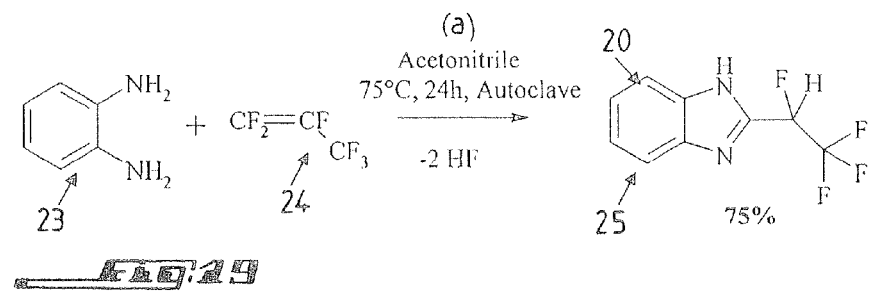
FIG. 19 illustrates the first step (a) of a method of producing a second protected monomer according to the invention.
Figure 20:
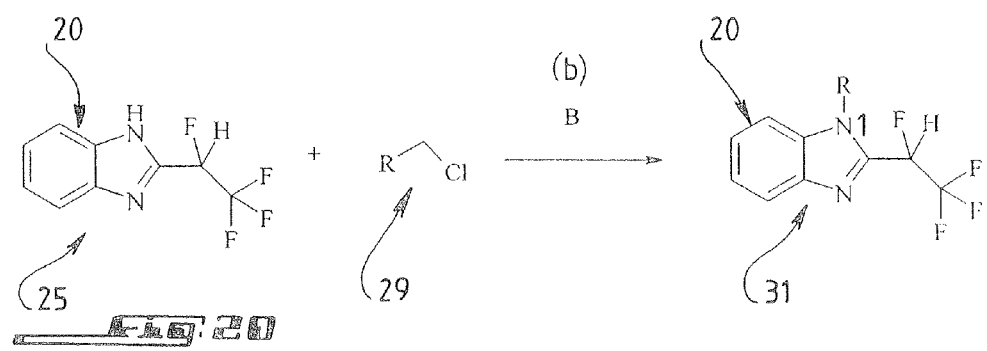
FIG. 20 shows the second step (b) of the method of producing the second protected monomer.
Figure 21:
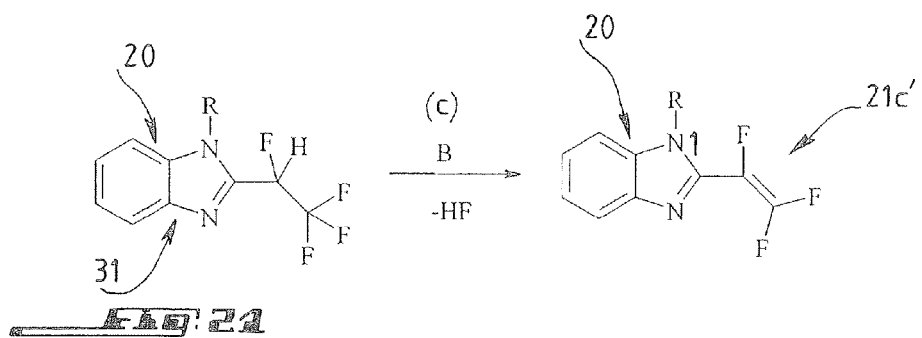
FIG. 21 represents the third step (c) of producing the second protected monomer.

This monomer 21c' can be obtained by a third production method in three steps, illustrated on FIGS. 19 to 21.

The first step (a) of FIG. 19, known by the person of the art and already illustrated on FIG. 15, concerns the reaction between ortho phenylene diamine 23 and hexafluoropropene 24 at 75° C. in acetonitrile, in autoclave and during 24 hours, from which the intermediate molecule 25, i.e., 2-(1,2,2,2-tetrafluoroethyl)-benzimidazole, results.

The output of this reaction is 75% after recrystallization in a $H_2O$/EtOH mixture.

The second step (b), represented on FIG. 20, is a reaction protecting one of the nitrogen atoms of the benzimidazole group 20 of the intermediate molecule 25, by means of a reagent 29 having the general formula RC1 where R can be a trialkylsilyl (R1R2R3Si) group or a carbamate group ($CO_2R1$).

The reaction is performed in a usual anhydrous organic solvent such as tetrahydrofurane (THF), dioxane or dimethylformamide (DMF) in the presence of a base B such as butyl lithium (BuLi), ter-butyl lithium (t-BuLi), lithium diisopropylamine (LDA) or sodium hydride (NaH).

By this reaction, a second intermediate compound 31 is obtained, whose nitrogen Ni is protected by the group R.

The third step (c) of the method, shown on FIG. 21, is a dehydrofluorination of compound 31 by means of a strong base such as butyl lithium (BuLi), ter-butyl lithium (t-BuLi), or lithium diisopropylamine (LDA) in an anhydrous solvent such as tetrahydrofurane (THF), dioxane or dimethylformamide (DMF).

This reaction makes it possible to obtain the monomer 21c' whose nitrogen atoms are protected by the group R, which is a trialkylsilyl or carbamate group.

Figure 22:
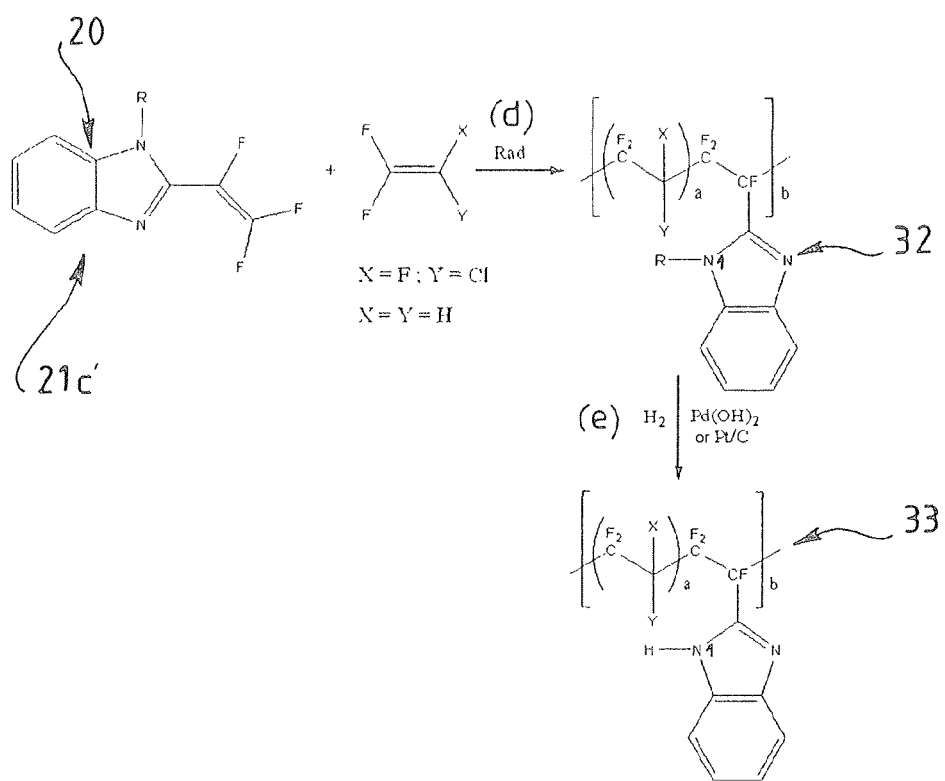
FIG. 22 illustrates the polymerization (d) of the protected monomer of FIG. 8 and the deprotection of the nitrogen atoms (e) of the protected polymer obtained at step (d).

As described for the case of the monomer 21b', the monomer 21c' thus obtained can be homopolymerized by radical initiation or copolymerized with fluorinated olefins as illustrated by step (d) of FIG. 22.

These fluorinated olefins can be constituted by hexafluoropropene (HFP), chlorotrifluoroethylene (CTFE), vinylidene fluoride (VDF), tetrafluoroethylene, trifluoroethylene, vinyl fluoride, or 2H-1,1,3,3,3-pentafluoroethylene.

By this step (d), a fluorinated polymer 32 is obtained, in which the nitrogen atoms of the heterocycles are protected by a group R.

This protected polymer 32 is then subjected to a deprotection step during which the groups R are replaced by hydrogen atoms, which enables the deprotected polymer 33 thus formed to be proton conductor.

In addition, the deprotected polymer obtained has a chemical inertia in oxidizing medium, because of the presence of fluorine atoms, and thermostability, because proton conduction is ensured by the anchored heterocycles, which predestines it to the production of membranes used in fuel cells.

It will be noted that the various monomers can be produced on the basis of steps (a), (b), and (c) of the above-described production method, by replacing the ortho phenylene diamine 23 of step (a) by a compound comprising such an ortho phenylene diamine 23, for example.

Similarly, other perhalogenated, fluorinated or partially fluorinated polymers can be formed from perhalogenated, fluorinated or partially fluorinated monomers carrying benzimidazole groups, then deprotected to form a proton conducting polymer.

As a consequence, several types of ionic conductive membranes can be produced from the deprotected perhalogenated polymers, to constitute different types of electrolytes, which can be integrated in many electrochemical devices, such as an electrolyzer, a fuel cell.

The membranes according to the invention make it possible in particular to go beyond the limit operating temperature of known fuel cells solid polymer electrolyte, to reduce the complexity of the fuel cell system (fuel cell and its auxiliaries), since the fuel cell according to the invention is anhydrous, and thus, as a consequence, its cost (auxiliaries dedicated to humidification are no longer necessary), and it has a longer life than usual fuel cells.

The heterocycles of the polymers formed according to the above-mentioned production methods ensure proton transport within the membrane, whereas the fluorinated groups present within the polymer provide the polymer with a certain chemical inertia in oxidizing or reducing medium and with thermostability, which participate in stabilizing the membrane during operation, in particular when used in a fuel cell operating at temperatures higher than 100° C.

The invention claimed is:

1. Monomer capable of being used for the production of an ionic conductive membrane, wherein said monomer has the formula:

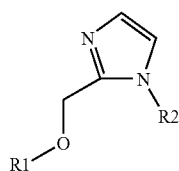

wherein
R1 has the chemical formula $(CH_2)_2$—O—CH=$CH_2$, and
R2 comprises a nitrogen atom-protection group, wherein the nitrogen atom-protection group is a benzyl or trialkylsilyl group.

2. Method of producing the monomer of claim 1 wherein R2 is benzyl, wherein said method comprises at least one step (a) of forming 1-benzyl-2-(hydroxymethyl)imidazole and at least one step (b) of synthesizing said monomer from this 1-benzyl-2-(hydroxymethyl)imidazole,
wherein the step of synthesizing the monomer includes
(i) a transetherification of the 1-benzyl-2-(hydroxymethyl)imidazole by ethyl vinyl ether, from which 1-benzyl-2-(vinyloxymethyl)imidazole results, or
(ii) a reaction between the 1-benzyl-2-(hydroxymethyl)imidazole and chloro ethyl vinyl ether in the presence of a phase transfer catalyst, from which 1-benzyl-2-(vinyloxyethyloxymethyl)imidazole results,
so as to obtain the monomer of claim 1 wherein R2 is benzyl.

3. Method according to claim 2, wherein the step of synthesizing the monomer is a transetherification of the 1-benzyl-2-(hydroxymethyl)imidazole by ethyl vinyl ether, from which 1-benzyl-2-(vinyloxymethyl)imidazole results, and the transetherification is performed in the presence of mercury acetate.

4. Method according to claim 2, wherein the step of synthesizing the monomer includes a reaction between the 1-benzyl-2-(hydroxymethyl)imidazole and chloro ethyl vinyl ether in the presence of a phase transfer catalyst, from which 1-benzyl-2-(vinyloxyethyloxymethyl)imidazole results, wherein the phase transfer catalyst is triethyl benzyl ammonium chloride.

5. Protected polymer comprising the monomer according to claim 1.

6. Protected polymer according to claim 5, wherein the polymer is an acid.

7. Method of producing a deprotected polymer using the protected polymer of claim 5, comprising a step of deprotecting the nitrogen atoms of the heterocycles of the protected polymer by which the protection groups (R2) of the polymer are replaced by hydrogen atoms, forming a deprotected polymer provided with heterocycles of the imidazole type.

8. Method according to claim 7, wherein the deprotection step comprises a reaction of the protected polymer obtained by the polymerization step with $Pd(OH)_2$.

9. Method of producing a protected polymer from the monomer of claim 1, comprising at least one step of polymerizing the monomer of claim 1.

10. Method according to claim 9, wherein the polymerization step comprises a cationic homopolymerization of the monomer in the presence of a cationic initiator.

11. Method according to claim 10, wherein the cationic initiator is selected from $ZnI_2$ and $HgI_2$.

12. Method according to claim 9, wherein the polymerization step comprises a radical copolymerization of this monomer with a second monomer.

13. Method according to claim 12, wherein the second monomer is an electron-accepting vinyl monomer.

14. Method according to claim 13, wherein the electron-accepting vinyl monomer is a fluorinated monomer.

15. Method according to claim 14, wherein the fluorinated monomer is selected from the family of fluorinated alkenes.

16. Method according to claim 9, wherein the polymerization step comprises a terpolymerization of the monomer with two other monomers.

17. Deprotected polymer, comprising a monomer having the formula:

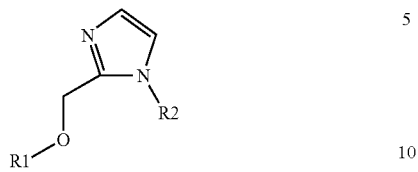

wherein
R1 has the chemical formula $(CH_2)_2$—O—CH=$CH_2$, and R2 is hydrogen.

18. Ionic conductive membrane comprising the deprotected polymer of claim 17.

19. Electrochemical device comprising the ionic conductive membrane of claim 18 as electrolyte.

20. Fuel cell comprising the ionic conductive membrane of claim 18 as electrolyte.

21. Electrolyzer comprising the ionic conductive membrane of claim 18 as electrolyte.

* * * * *